United States Patent
Broekaert et al.

(10) Patent No.: US 9,845,365 B2
(45) Date of Patent: Dec. 19, 2017

(54) METHOD FOR MAKING PENTOSES AND PENTOSE-BASED SOLUBLE OLIGO/POLYSACCHARIDES FROM CEREAL GRAIN INVOLVING DEBRANNING TECHNOLOGY

(71) Applicant: Cargill, Incorporated, Wayzata, MN (US)

(72) Inventors: Willem Broekaert, Dilbeek (BE); Jan Delcour, Heverlee (BE); Wim Veraverbeke, Heverlee (BE)

(73) Assignee: CARGILL, INCORPORATED, Wayzata, MN (US)

( * ) Notice: Subject to any disclaimer, the term of this patent is extended or adjusted under 35 U.S.C. 154(b) by 0 days.

(21) Appl. No.: 14/429,650

(22) PCT Filed: Sep. 19, 2013

(86) PCT No.: PCT/US2013/060654
§ 371 (c)(1),
(2) Date: Mar. 19, 2015

(87) PCT Pub. No.: WO2014/047312
PCT Pub. Date: Mar. 27, 2014

(65) Prior Publication Data
US 2015/0225489 A1    Aug. 13, 2015

(30) Foreign Application Priority Data
Sep. 20, 2012 (GB) .................................. 1216767.2

(51) Int. Cl.
| | |
|---|---|
| C08B 37/00 | (2006.01) |
| C08B 30/02 | (2006.01) |
| C08H 99/00 | (2010.01) |
| C08L 5/00 | (2006.01) |
| C12P 19/02 | (2006.01) |
| C12P 19/14 | (2006.01) |

(52) U.S. Cl.
CPC .......... *C08B 37/0087* (2013.01); *C08B 30/02* (2013.01); *C08B 37/0003* (2013.01); *C08B 37/0057* (2013.01); *C08H 99/00* (2013.01); *C08L 5/00* (2013.01); *C12P 19/02* (2013.01); *C12P 19/14* (2013.01)

(58) Field of Classification Search
CPC ..................................................... C08B 30/02
See application file for complete search history.

(56) References Cited

FOREIGN PATENT DOCUMENTS

| | | |
|---|---|---|
| WO | 0167891 A1 | 9/2001 |
| WO | 2011138303 A1 | 11/2011 |

OTHER PUBLICATIONS

Trogh et al. J. Agric. Food Chem., 2005, 53:7243-7250.*
Dervilly-Pinel et al. J of Cereal Science, 2001, 34:207-214.*
International Search Report. PCT/US2013/060654, dated Oct. 29, 2014, 4 pgs.
Katrien Swennen et al: "Large-Scale Production and Characterisation of Wheat Bran Arabinoxylooligosaccharides", Journal of the Science of Food and Agriculture, vol. 86, 2006, pp. 1722-1731, XP002457409.
Hemery et al.: "Dry Processes to Develop Wheat Fractions and Products With Enhanced Nutritional Quality", Journal of Cereal Science, Academic Press Ltd., vol. 46, 2007, pp. 327-347, XP022316979.
Buri R.C. et al.: "Description and Characterization of Wheat Aleurone", vol. 49, 2004, pp. 274-282, XP008131409.
Lempereur I., et al. "Genetic and Agronomic Variation in Arabinoxylan and Ferulic Acid Contents of Durum Wheat (Triticum Durum L.) Grain and it's Milling Fractions", Journal of Cereal Science, 1997, pp. 103-110, XP056084504

* cited by examiner

*Primary Examiner* — Bin Shen

(57) ABSTRACT

The present invention provides a method for the extraction and isolation of soluble arabinoxylan products from cereal grain. Preferably, such soluble arabinoxylan product is any one of soluble arabinoxylan, arabinoxylan-oligosaccharides, xylose, arabinose, ferulic acid and mixtures thereof. Said method comprises partial debranning of whole cereal grains to obtain partially debranned cereal grains followed by roller milling of said partially debranned cereal grains to obtain cereal bran. The method further comprises the mashing of at least part of said cereal bran in water optionally involving the treatment of the mash with any one of an enzyme preparation, an acid, a base, a peroxide or combinations thereof, either simultaneously or sequentially, to solubilize and optionally depolymerize a fraction of the arabinoxylan comprised in said cereal bran. Preferably, said treatment is done with an enzyme preparation containing an endoxylanase. The method further comprises the separation from said mash of a solubilized fraction, which comprises at least part of the solubilized soluble arabinoxylan products.

26 Claims, No Drawings

METHOD FOR MAKING PENTOSES AND PENTOSE-BASED SOLUBLE OLIGO/POLYSACCHARIDES FROM CEREAL GRAIN INVOLVING DEBRANNING TECHNOLOGY

CROSS-REFERENCE TO RELATED APPLICATION

This application is a national phase application of International Application No. PCT/US2013/060654, Filed 19 Sep. 2013, entitled METHOD FOR MAKING PENTOSES AND PENTOSE-BASED SOLUBLE OLIGO/POLYSACCHARIDES FROM CEREAL GRAIN INVOLVING DEBRANNING TECHNOLOGY, which claims the benefit of Great Britain Application No. 1216767.2, 20 Sep. 2012, entitled METHOD FOR MAKING PENTOSES AND PENTOSE-BASED SOLUBLE OLIGO/POLYSACCHARIDES FROM CEREAL GRAIN INVOLVING DEBRANNING TECHNOLOGY, which are hereby incorporated by reference in their entirety.

FIELD OF THE INVENTION

The present invention relates to a method for the extraction and isolation from cereal grain of soluble arabinoxylan products, such as pentoses and/or soluble pentose-based oligo/polysaccharides, which can be used as food, beverage, cosmetics or feed ingredients or as substrates for fermentation or chemical modifications.

BACKGROUND OF THE INVENTION

Arabinoxylans (AX) are an important constituent of the cell walls of cereal grains. AX are carbohydrates consisting of a backbone of β-1,4-linked D-xylopyranoside (xylose) units that are either unsubstituted, monosubstituted with a single α-L-arabinofuranoside (arabinose) at either C—(O)-2 or C—(O)-3, or disubstituted with single α-L-arabinofuranoside units at C—(O)-2 and C—(O)-3 (Izydorczyk and Biliaderis, 1995; Andersson and Aman, 2001;). The pentoses xylose and arabinose are thus the main building blocks of AX, and AX are therefore also called pentosans. Less abundant substituents attached to the C—(O)-2 position of the xylose units can be glucuronic acid, 4-O-methyl glucuronic acid, or short oligomers consisting of L-arabinose, D-xylose, D-galactose, D-glucose and/or uronic acids, while acetyl groups can be linked to the C—(O)-2 and/or C—(O)-3 position of the xylose units. Hydroxycinnamic acids, mainly ferulic acid, and to a lesser extent dehydrodiferulic acid, p-coumaric acid, and sinapic acid, are present as substituents as well, and they are generally linked to the C—(O)-5 position of terminal arabinose units (Izydorczyk and Biliaderis, 1995; Andersson and Aman, 2001).

Apart from their common structural feature of a xylose backbone substituted with arabinose, cereal grain AX constitute a very heterogenous group of carbohydrates. Large variations in degree of arabinose substitution and nature and frequency of the less abundant substituents have been observed, not only when comparing different cereal species but also when comparing different tissues within a single cereal species (Antoine et al., 2003; Barron et al., 2007). It is generally conceded that cereal AX have a degree of polymerisation (DP) between 1,500 and 15,000, although it is difficult to determine their exact molecular weight because of the partial degradation that typically takes place during their extraction and purification (Broekaert et al., 2011).

Overall, cereal grains contain between 5 and 10% of AX. However, AX are not evenly distributed over the different tissues of the cereal grain. Particularly the outer layers of the cereal grain are rich in AX, explaining the common practice to first physically fractionate the cereal grain to obtain a fraction enriched in the outer layers (commonly named "bran") to serve as raw material for the preparation of AX derived products. However, the major part of the AX from the outer layers of the cereal grain are water-unextractable and cannot be isolated in their native state because they are intimately associated with other cell wall materials by both covalent and non-covalent interactions. As a result, isolation of a substantial fraction of the AX from bran often involves at least partial hydrolytic depolymerisation of the AX. Furthermore, this depolymerisation of the AX is mostly also desirable from an application point of view. Indeed, the high viscosity that comes with the high molecular weight of AX is often not desired for many applications of AX.

Depending on their DP, solubilised AX depolymerisation products find their way in different applications. For instance, arabinoxylan-oligosaccharides (AXOS) have recently been shown to exert prebiotic properties (Cloetens et al., 2008; Courtin et al., 2008; Van Craeyveld et al., 2008; Broekaert et al., 2011). AXOS containing preparations therefore have a wide potential as ingredient in food, beverage and feed applications. AX can also be used as an ingredient for cosmetics. The pentoses xylose and arabinose could be used for fermentation, for instance for the production of ethanol, if yeast strains are engineered such that they can utilise and ferment xylose and arabinose (Hahn-Hägerdal et al., 2007). The pentose xylose can be used in applications in the pharmaceutical, cosmetic and food industry, and as a substrate for enzymatic or chemical conversion to xylitol, which can be used as a non-cariogenic sweetener. The pentose arabinose is widely used as an intermediate in the production of pharmaceuticals, such as nucleoside analogue antiviral agents.

Several methods have been described to prepare pentoses or pentose-based oligosaccharides from cereal bran.

AX depolymerisation products can be prepared from cereal bran by aqueous extraction in the presence of endoxylanase enzymes (WO 02/067698; WO 2006/027529; Maes et al., 2004; Swennen et al., 2006). These methods have the benefit of being based on gentle extraction conditions; however, recoveries of AX are typically limited due to the inaccessibility of an important part of the cereal bran AX to the enzymes.

Higher recoveries can be obtained with alkaline extraction conditions (U.S. Pat. No. 3,879,373; WO 98/31713). Extraction methods that combine alkali with peroxide (Maes and Delcour, 2001; Hollmann and Lindhauer, 2005) have been described as well. The main drawback of these methods is that the extraction step with high concentration of alkali is environment-unfriendly, and requires costly removal of the chemicals from the different product streams. Furthermore, the AX extracted with alkaline solutions have a high molecular weight and an additional endoxylanase treatment (Yamada et al., 1993; Beaugrand et al., 2004) is generally still required to obtain AX depolymerisation products with a desired molecular weight. Finally, the AX extracted with alkaline solutions are devoid of hydroxycinnamic acid substituents (Hollmann and Lindhauer, 2005), most likely due to saponification of the ester link. The lack of hydroxycinnamic acid substituents can be a drawback for the use of such preparations in food and cosmetics applications, since the hydroxycinnamic acid substituents confer desired antioxidant properties to the AX or AXOS (Ohta et al., 1997; Yuan et al., 2005; Vitaglione et al., 2008).

Higher recoveries can also be obtained with acidic extraction conditions. Different extraction methods with acid solutions at high temperature have been described (Sanjust et al., 2004; Palmarola-Adrados et al., 2005; WO 2010/088744). However, these methods are generally more suited to produce pentoses rather than pentose-based oligosaccharides, due to extensive acid-catalysed hydrolysis of the polysaccharide links.

Finally, high recoveries can be obtained in aqueous solutions using a hydrothermal treatment at high pressure and high temperature leading to autohydrolysis of AX (Garrote et al., 2002; Kabel et al., 2002; Carvalheiro et al., 2004; Rose and Inglett, 2010). A potential drawback of this treatment is the release of substantial amounts of free monosaccharides which may not always be desired. Furthermore, the conditions leading to autohydrolysis of AX, also lead to the formation of pentose degradation products such as furfural.

Bran is conventionally produced as a by-product of milling of cereal grain using a roller mill. In a roller mill, the cereal grain is ground by the action of pairs of rolls rotating in opposite direction and sieves are used for separation of ground cereal grain fractions. Bran produced by roller milling comprises a range of different tissues, including pericarp, seed coat, nucellar epidermis, aleurone as well as minor parts of the starchy endosperm (Delcour and Hoseney, 2010). It is known that these different tissues not only do have different contents of AX, the AX from the different tissues also differ in structure and hence in accessibility by endoxylanases. More particularly, the lesser arabinose substituted AX from the aleurone and nucellar epidermis appear to be well solubilised by the action of endoxylanases while this is much less the case for the more complex AX from the pericarp (Benamrouche et al., 2002; Ordaz-Ortiz at al., 2005; Van Craeyveld et al., 2010).

Another method for producing cereal bran is debranning. Debranning is the controlled removal of peripheral layers of cereal grain while leaving the remaining cereal grain substantially intact. Debranning can be done by friction (peeling), i.e. the rubbing of cereal grains against each other, or by abrasion (pearling), i.e. the rubbing of cereal grains against an abrasive surface, or by a combination of both (Hemery et al., 2007).

It is an object of the present invention to provide more cost efficient methods for the extraction and isolation of soluble AX products from cereals than the methods known from the prior art. The higher cost efficiency is based on alternative methods to prepare bran from cereal grain that result in higher yields from bran in the preparation of the soluble AX products. It was unexpectedly found that, while higher yields were not obtained with bran obtained by debranning of cereal grain compared to bran obtained by roller milling, higher yields were obtained with bran prepared by roller milling of partially debranned cereal grain.

SUMMARY OF THE INVENTION

The present invention provides a method for the extraction and isolation of soluble arabinoxylan products from cereal grain. Preferably, such soluble arabinoxylan product is any one of soluble arabinoxylan, arabinoxylan-oligosaccharides, xylose, arabinose, ferulic acid and mixtures thereof. Said method comprises partial debranning of whole cereal grains to obtain partially debranned cereal grains followed by roller milling of said partially debranned cereal grains to obtain cereal bran. The method further comprises the mashing of at least part of said cereal bran in water optionally involving the treatment of the mash with any one of an enzyme preparation, an acid, a base, a peroxide or combinations thereof, either simultaneously or sequentially, to solubilise and optionally depolymerise a fraction of the arabinoxylan comprised in said cereal bran. Preferably, said treatment is done with an enzyme preparation containing an endoxylanase. The method further comprises the separation from said mash of a solubilised fraction, which comprises at least part of the solubilised soluble arabinoxylan products.

DETAILED DESCRIPTION

Definitions

In the context of the present invention, the term "cereal" refers to plants of the botanical family of the Poaceae, including but not limited to species such as (*durum*) wheat, triticale, barley, oats, rye, sorghum, maize, and rice.

In the context of the present invention, the terms "cereal grain" or "grain" refer to the native kernel-like fruits of cereal plants, also known as caryopsis, and comprising the pericarp, seed coat, nucellar epidermis, aleurone, starchy endosperm and germ tissues. In the context of the present invention, the terms "cereal grain" or "grain" also refer to the material remaining when outer layers are removed from native kernel-like fruits of cereal plants while leaving the kernel-like structure of the remaining inner layers substantially intact. In the context of the present invention, the terms "whole cereal grains" or "whole grains" refers to cereal grains, which have not been subject to any processing involving the removal of relevant amounts of the outer grain layers. In consequence, such "whole cereal grains" or "whole grains" comprise a substantially intact pericarp and seed coat.

In the context of the present invention, the terms "cereal bran" or "bran" refer to a cereal grain fraction that (a) is substantially enriched in any or all of the tissues to be selected from pericarp, seed coat, nucellar epidermis, and aleurone compared with the cereal grain from which it is derived and/or (b) has a substantially lower starch content than the cereal grain from which it is derived.

In the context of the present invention, the terms "cereal flour" of "flour" refer to a ground cereal grain fraction that (a) is substantially enriched in starchy endosperm tissue compared with the cereal grain from which it is derived and/or (b) has a substantially higher starch content than the cereal grain from which it is derived.

In the context of the present invention, the term "roller milling" refers to any method to grind cereal grain and separate the ground cereal grain into at least one bran fraction and one flour fraction. The method is further characterised in that pairs of rolls rotating in opposite direction are used for grinding of the cereal grain and that sieves are used for separation of ground cereal grain fractions.

In the context of the present invention, the term "debranning" refers to any method for removing outer layers from cereal grains without milling or otherwise grinding the cereal grain, preferably with minimal or no damage or alteration of the underlying cereal grain layers, i.e. for instance with minimal breakage of the cereal grain or minimal pitting or scratching of said underlying layers of the cereal grain. Examples of debranning techniques are peeling (removal based on friction between cereal grains) and pearling (removal based on abrasion between cereal grains and an abrasive mechanical surface).

In the context of the present invention, the term "partial debranning" refers to any debranning method that yields a cereal grain from which a substantial amount of bran can be obtained by either subsequent roller milling or subsequent debranning.

In the context of the present invention, the terms "partially debranned cereal grain" or "partially debranned grain", abbreviated as DBG, refers to cereal grain that is obtained by partial debranning of cereal grain.

In the context of the present invention, the term "debranning bran", abbreviated as DBB, refers to bran that is obtained by debranning of cereal grain.

In the context of the present invention, the term "roller milling bran", abbreviated as RMB, refers to bran that is obtained by roller milling of cereal grain.

In the context of the present invention, the term "median particle size" refers to the $50^{th}$ percentile particle size ($D_{50}$), i.e. the value on the particle size distribution by mass such that 50% of the mass of the particles have a diameter of this value or less. Preferably, the particle size distribution is determined through standard sieve analysis involving a nested column of a series of sieves with different wire mesh screens.

In the context of the present invention, the term "endoxylanase" refers to an enzyme that is able to hydrolyse internal glycosyl bonds linking xylose units in xylose-containing polysaccharides. Such glycosyl bonds can be for instance the β-1,4-glycosyl bond in β-D-xylopyranosyl-1,4-δ-D-xylopyranosyl units of such polysaccharides. Endoxylanases can be derived from a variety of organisms, including plant, fungal (e.g. species of *Aspergillus, Penicillium, Disporotrichum, Neurospora, Fusarium, Humicola, Trichoderma*) or bacterial species (e.g. species of *Bacillus, Aeromonas, Streptomyces, Nocardiopsis, Thermomyces, Thermotoga*) (see for example WO92/17573, WO92/01793, WO91/19782, WO94/21785). Commercially available purified or partially purified endoxylanase preparations include but are not limited to Frimase™ B210 (Puratos), Shearzyme™ (Novozymes), Biofeed Wheat™ (Novozymes), Pentopan™ Mono BG (Novozymes), Pentopan™ 500 BG (Novozymes), Pulpzyme™ (Novozymes), Ecopulp™ (AB Enzymes), Veron™ 191 (AB Enzymes), Veron™ Special (AB Enzymes), Multifect™ CX12L (Genencor/Danisco), Spezyme™ CP (Genencor/Danisco), Grindamyl™ H640 (Danisco), and Grindamyl™ Powerbake™ (Danisco).

In the context of the present invention, the term "arabinoxylan", abbreviated as AX, refers to polymers consisting of a backbone of β-1,4-linked D-xylopyranoside (xylose) units with a degree of polymerisation of the backbone above 100. The xylose units are either unsubstituted, monosubstituted with a single α-L-arabinofuranoside (arabinose) unit at either C—(O)-2 or C—(O)-3, or disubstituted with single α-L-arabinofuranoside units at C—(O)-2 and C—(O)-3. Other substituents such as acetyl, α-glucuronyl, α-4-O-methylglucuronyl, galacturonyl, xylosyl, rhamnosyl, galactosyl, or glucosyl side chains, or short oligosaccharide side chains, can be attached to one or more of the xylose units and hydroxycinnamic acids, such as ferulic acid, dehydrodiferulic acid, p-coumaric acid, caffeic acid or sinapic acid, can be linked to one or more of the arabinose units.

In the context of the present invention, the term "arabinoxylan-oligosaccharides", abbreviated as AXOS, refers to either xylo-oligosaccharides or arabino-xylo-oligosaccharides, or mixtures of xylo-oligosaccharides and arabino-xylo-oligosaccharides. Xylo-oligosaccharides refers to poly- or oligosaccharides consisting solely of unsubstituted β-(1-4)-linked D-xylopyranosyl (xylose) units with a degree of polymerisation between 2 and 100. Arabino-xylo-oligosaccharides refers to poly- or oligosaccharides consisting of a backbone of β-(1-4)-linked D-xylopyranosyl (xylose) units with a degree of polymerisation of the backbone between 1 and 100, with at least one α-L-arabinofuranosyl (arabinose) unit linked to one of the xylose units of the backbone per molecule. Other substituents such as acetyl, α-glucuronyl, α-4-O-methylglucuronyl, galacturonyl, xylosyl, rhamnosyl, galactosyl, or glucosyl side chains, or short oligosaccharide side chains, can be attached to one or more of the xylose units and hydroxycinnamic acids, such as ferulic acid, dehydrodiferulic acid, p-coumaric acid, caffeic acid or sinapic acid, can be linked to one or more of the arabinose units.

In the context of the present invention, the term "AX(OS)", refers to both AX and AXOS as defined above.

In the context of the present invention, the term "arabinoxylan depolymerisation products" refers to arabinoxylan-oligosaccharides, xylose, arabinose and hydroxycinnamic acids, such as ferulic acid, or to mixtures thereof.

In the context of the present invention, the term "soluble arabinoxylan products" refers to soluble arabinoxylans, arabinoxylan depolymerisation products or to mixtures thereof.

In the context of the present invention, the term "α/β-glucan" refers to either α-glucan or β-glucan, or mixtures of α-glucan and β-glucan. α-glucan refers to poly- or oligosaccharides consisting of α-(1-4)- and/or α-(1-6)-linked D-glucopyranosyl (glucose) units with a degree of polymerisation equal or above 2, including but without limitation, starch, amylose, amylopectin, maltodextrin, maltose or mixtures thereof. β-glucan refers to non crystalline poly- or oligosaccharides consisting of β-(1-3)- and/or β-(1-4)-linked D-glucopyranosyl (glucose) units with a degree of polymerisation equal or above 2. In the context of the present invention, the term "α/β-glucan" also refers to poly- or oligosaccharides consisting of linked D-glucopyranosyl (glucose) units with a degree of polymerisation equal or above 2, that are fully hydrolysed to glucose during 1 hour incubation at 110° C. in 2 N trifluoro acetic acid.

In the context of the present invention, the terms "soluble" or "solubilised" refer to soluble in water as the solvent or solubilised in water as the solvent, respectively.

Description

Soluble arabinoxylans and arabinoxylan depolymerisation products are used as an ingredient in food, feed and cosmetic applications. Furthermore, they provide intermediate compounds for the chemical and pharmaceutical industry. Cereal bran, in particular wheat, rye and oat bran, is a good source of arabinoxylans. However, as explained above there is a need for techniques allowing an efficient extraction of these arabinoxylans and arabinoxylan depolymerisation products, while avoiding harsh extraction conditions.

It is an object of the present invention to provide a method for the extraction and isolation of soluble arabinoxylan products from cereal grain. In a first step said method comprises partial debranning of whole cereal grains in order to remove part of the outer layers from said whole cereal grains, yielding a first cereal bran and partially debranned cereal grains. Preferably, said partial debranning results in the production of an amount of said first cereal bran corresponding to at least 2% (w/w), preferably at least 4% (w/w), such as for instance at least 5, 6 or 7% (w/w) of the initial weight of the whole cereal grains. It is further preferred that said partial debranning results in the production of an amount of said first cereal bran corresponding to at most 15% (w/w), preferably at most 13% (w/w), such as for instance at most 12% or 10% (w/w) of the initial weight of the whole cereal grains. It is also preferred that said partial debranning of the whole cereal grains results in the production of an amount of partially debranned cereal grains corresponding to at least 85% (w/w), such as at least 90% (w/w) of the initial weight of the whole cereal grains. It is further preferred that said partial debranning results in the production of an amount of said partially debranned cereal grains corresponding to at most 98% (w/w), preferably at most 96% (w/w), such as for instance at most 95, 94 or 93% (w/w) of the initial weight of the whole cereal grains. Considering that said partial debranning of the whole cereal grains aims at removing at least part of the outer layers from said cereal grains, it is preferred that said first cereal bran is particularly rich in pericarp material.

Subsequently, said partially debranned cereal grains are roller milled yielding a second cereal bran and cereal flour. Said second cereal bran or a part or fraction thereof is then mashed in an aqueous solution in order to solubilise and possibly depolymerise at least part of the arabinoxylan contained therein. The method may optionally involve the treatment of said mash with any one of an enzyme preparation, an acid, a base, a peroxide or combinations thereof, either simultaneously or sequentially. Optionally, prior to its mashing said second cereal bran is dry milled or ground otherwise. Preferably, said second cereal bran is ground to obtain a cereal bran with a median particle size smaller than 1000 µm, more preferably smaller than 750 µm, such as smaller than 500 µm. It is further preferred that the median particle size of said ground second cereal bran is 250 µm or more, such as for instance 300 or 350 µm or more. Such grinding of said cereal bran may involve the use of a hammer mill or other suitable grinding equipment. In the frame of the present invention it was observed that the bran particles in said second cereal bran or ground second cereal bran with a particle size smaller than 250 µm, such as smaller than 150 µm, or smaller than 100 µm, are relatively rich in starch and low in arabinoxylan compared to bran particles with a particle size higher than 250 µm. Therefore, it may be advantageous that, prior to its mashing, said second cereal bran or said ground second cereal bran is fractionated, using for instance sieving or air classification, in order to remove a significant part of the bran particles with a particle size smaller than 250 µm, preferably to remove a significant part of the particles smaller than 150 µm, such as for instance to remove a significant part of the particles smaller than 100 µm. Preferably, said fractionation results in a reduction of the weight fraction of the particles smaller than 250 µm in said second cereal bran or ground second cereal bran after fractionation by at least 40% (w/w), more preferably at least 60% (w/w), such as at least 70% (w/w) or 80% (w/w) as compared to said weight fraction in the second cereal bran or ground second cereal bran before fractionation. More preferably, said fractionation results in a reduction of the weight fraction of the particles smaller than 150 µm in said second cereal bran or ground second cereal bran after fractionation by at least 50% (w/w), more preferably at least 70% (w/w), such as at least 80% (w/w) or 90% (w/w) as compared to said weight fraction in the second cereal bran or ground second cereal bran before fractionation. The removal of these smaller particles with a relatively low arabinoxylan content from said (ground) second cereal bran increases the extraction efficiency and yield of the soluble arabinoxylan products.

In order to favour the extraction of the soluble arabinoxylan products from the mashed second cereal bran material, it is preferred that after mashing of said bran material the mash is incubated during a period of at least 1 hour, more preferably at least 4 hours, such as at least 6 hours. It is further preferred that the incubation time of the mash is at most 24 hours, such as at most 12 hours or 10 hours. In case the method of the present invention is used for the purpose of producing arabinoxylan depolymerisation products, it is advised that an endoxylanase enzyme preparation is added to said aqueous solution wherein said bran is mashed. More preferably, said added endoxylanase enzyme preparation comprises an endoxylanase with high selectivity for water-unextractable arabinoxylan, such as an endoxylanase of the glycosyl hydrolase family 11.

The method of the present invention further comprises the separation of a solubilised fraction, which comprises at least part of the soluble arabinoxylan products, from the insoluble material in said mash.

Preferably, said solubilised fraction is further processed using filtration or chromatography techniques or combinations thereof, in order to reduce the presence of suspended solids, or to reduce the presence of impurities such as minerals and proteins. It may also be advantageous to further separate said solubilised fraction into two or more fractions that differ in free ferulic acid content, arabinose to xylose ratio or average degree of polymerisation of the soluble arabinoxylan products.

Optionally, an enzyme preparation comprising an endoxylanase enzyme is added to the solubilised fraction in order to decrease the average degree of polymerisation of the soluble arabinoxylan products.

It is preferred that such solubilised fraction comprising soluble arabinoxylan products is eventually concentrated in order to increase its dry substance concentration. It is further preferred that such solubilised fraction or such concentrated solubilised fraction is crystallised or dried, in order to obtain a substantially dry product.

In a particular embodiment, said second cereal bran or a part or fraction thereof used for extracting and isolating the soluble arabinoxylan products is treated to lower the presence of minerals and/or to lower the presence of starch and/or protein derived products in the eventual solubilised fraction comprising the soluble arabinoxylan products. Typically, this is done by mashing and incubating said second cereal bran material in a first aqueous solution. Optionally, either or both an enzyme preparation comprising amylase activity and an enzyme preparation comprising protease activity are added to said first aqueous solution in order to solubilise at least part of the starch and protein material contained in said second cereal bran. Subsequent to the mashing and incubation of said second cereal bran material in said first aqueous solution, at least part of the solubilised material is separated and the remaining non-solubilised bran material is mashed in a second aqueous solution in order to solubilise and optionally depolymerise at least part of the arabinoxylan contained in said bran material. In order to favour the solubilisation of the arabinoxylan from said bran material, it is preferred that after mashing of said bran material the mash is incubated during a period of at least 1 hour, more preferably at least 4 hours such as at least 6 hours. It is further preferred that the incubation time of the mash is at most 24 hours, such as at most 12 or 10 hours. In case, the method of the present invention according to this embodiment is used for the purpose of producing arabinoxylan depolymerisation products, it is advised that an endoxylanase enzyme preparation is added to said second aqueous solution. More preferably, said added endoxylanase enzyme preparation comprises an endoxylanase with high selectivity for water-unextractable arabinoxylan, such as an endoxylanase of the glycosyl hydrolase family 11. The method of the present invention according to the present embodiment further comprises the separation of a solubilised fraction, which comprises at least part of the soluble arabinoxylan products, from the insoluble material in said mash. Thereafter, said solubilised fraction may be further processed, concentrated and/or dried as previously described.

The solubilised fraction obtained according to the method of the present invention typically comprises at least 20% (w/w) soluble arabinoxylan products on a dry weight basis, more preferably it comprises at least 40% (w/w), such as for instance at least 60% (w/w) or at least 70% (w/w) soluble arabinoxylan products on a dry weight basis.

Illustrative Embodiment

Example 1: Effect of Debranning Prior to Roller Milling in Wheat Bran Production on Arabinoxylan Solubilisation of Wheat Bran Debranning Wheat grains from the region of Northern France were cleaned by sieving on a 3360 μm sieve to remove large impurities, such as straw and unthreshed wheat (cleaned wheat grains pass through sieve) and on a 2380 μm sieve to remove small impurities and broken grains (cleaned wheat grains stay on sieve). Moisture content of the wheat grains was 12.3% (w/w) and was not adjusted before debranning.

Cleaned wheat grains were debranned on a Satake VAF 10AM Debranner in multiple passes. In each pass, approximately 5% (w/w) of the wheat grains was removed. In between passes, debranned wheat grains were cleaned on a 2380 μm sieve to remove broken grains and fragments resulting from the debranning process (non broken wheat grains stay on sieve). Actual removal rates during debranning and sieving steps are shown in Table 1. Debranning thus resulted in bran samples DBB 0-5, ORB 5-10, DBB 10-15 and in partially debranned grain samples DBG 5+ and DBG 10+, as indicated in Table 1.

Roller Milling

Cleaned untreated and the partially debranned grain samples DBG 5+ and DBG 10+ were roller milled on a Bühler MLU 202 laboratory scale mill after adjusting wheat grain moisture contents (overnight incubation) to the levels shown in Table 2. Three different milling fractions (coarse bran, fine bran and flour) were collected from each wheat grain sample. Coarse bran consists of particles >530 μm, substantially derived from pericarp, seed coat, nucellar epidermis and aleurone tissues of the original grain. Fine bran consists of particles between 530 μm and 150 μm, substantially derived from pericarp, seed coat, nucellar epidermis, aleurone and starchy endosperm tissues of the original grain. Flour consists of particles <150μ, substantially derived from the starchy endosperm tissue of the original grain. Levels of the different milling fractions obtained from the different wheat grain samples are shown in Table 2. As indicated in Table 2, six different bran preparations were selected for further work. These were the coarse bran fractions (RMB 0-11, RMB 5-11 and RMB 10-14), collected from each of the three wheat grain samples and mixtures of coarse and fine bran (RMB 0-23, RMB 5-25 and RMB 10-27; mixed in the ratios as obtained from milling) also collected from each of the three wheat grain samples.

Characterisation of Bran Preparations

AX(OS) content, α/β-glucan content and A/X ratio of the nine bran preparations obtained by debranning and/or roller milling of wheat grain were determined by gas-liquid chromatography.

The total saccharide content was determined by gas-liquid chromatographic analysis of the alditol acetates after acid hydrolysis of the samples in 2 N trifluoroacetic acid, followed by reduction with sodium borohydride and acetylation with acetic anhydride, as described by Courtin et al. (2000). β-D-Allose was used as internal standard and calibration samples, containing the monosaccharides D-glucose, D-galactose, D-mannose, D-xylose and L-arabinose, were included with each set of samples. The reducing end saccharide content was determined by gas-liquid chromatographic analysis of the alditol acetates after reduction with sodium borohydride, followed by acid hydrolysis and acetylation with acetic anhydride, as described by Courtin et al. (2000). The procedure for the analysis of free monosaccharide content was very similar to that of total saccharides (Courtin et al., 2000), with the only difference that samples were not hydrolysed prior to reduction and acetylation to alditol acetates.

From the total saccharide, reducing end saccharide and free monosaccharide contents, AX(OS) content, α/β-glucan content and A/X ratio were calculated according to the below formulae (a), (b) and (c), respectively.

$$AX(OS) \text{ content} = 0.88 \times [\text{arabinose}_{TOT} - \text{arabinose}_{FREE}] + [\text{xylose}_{RED} - \text{xylose}_{FREE}] + 0.88 \times [\text{xylose}_{TOT} - \text{xylose}_{RED}] \quad (a)$$

$$\alpha/\beta\text{-glucan content} = 0.90 \times [\text{glucose}_{TOT} - \text{glucose}_{FREE}] \quad (b)$$

$$A/X \text{ ratio} = [\text{arabinose}_{TOT} - \text{arabinose}_{FREE}] / [\text{xylose}_{RED} - \text{xylose}_{FREE}] \quad (c)$$

In the above formulae, the subscripts TOT, RED and FREE refer to total saccharide, reducing end saccharide and free monosaccharide contents, respectively, and the factors 0.88 and 0.90 correct for the incorporation of water during hydrolysis of pentose sugars and hexose sugars, respectively (Femia et al., 2010). All contents are expressed as % of dry matter (% dm).

AX(OS) content, α/β-glucan content and A/X ratio of the bran preparations produced in Example 1 are shown in Table 3.

The compositions of the "debranning bran" preparations obtained by debranning of wheat grain (DBB 0-5, DBB 5-10 and DBB 10-15) illustrate that when outer layers of wheat grain are gradually removed, they gradually contain less AX(OS) and more α/β-glucan and have a lower A/X ratio (Table 3). While the first 5% (w/w) debranning bran fraction of wheat grain (DBB 0-5) contains more AX(OS) and less α/β-glucan than bran obtained by traditional roller milling of wheat grain (RMB 0-11 and RMB 0-23), its A/X ratio is much higher than those of the traditional bran preparations. In contrast, the A/X ratios of subsequent 5% (w/w) debranning bran fractions of wheat grain (DBB 5-10 and DBB 10-15) are comparable or even slightly lower than those of the traditional bran preparations (RMB 0-11 and RMB 0-23). However, their AX(OS) contents are much lower and their α/β-glucan contents are much higher than those of the traditional bran preparations. High α/β-glucan levels of bran negatively affect the purity of soluble AX(OS) preparations or lead to higher efforts (higher costs) to obtain the same purity of the soluble AX(OS) preparations.

"Roller milling bran" preparations obtained by roller milling of (debranned) wheat grain significantly differ in composition depending on the choice whether to include the "fine bran" wheat milling fraction in the sample or not. Table 3 shows that irrespective of the nature of the wheat grain starting material used for roller milling, addition of the "fine bran" to the "coarse bran" always results in bran preparations with lower AX(OS) contents, higher α/β-glucan contents and higher A/X ratios than the corresponding bran preparations consisting of only "coarse bran" (compare RMB 0-23 with RMB 0-11, RMB 5-25 with RMB 5-11 and RMB 10-27 with RMB 10-14 in Table 3).

Table 3 further shows that debranning of wheat grain prior to roller milling has a clear effect on the composition of the roller milling bran samples. Debranning prior to roller milling generally results in roller milling bran preparations with lower AX(OS) content, higher α/β-glucan content and lower A/X ratio than roller milling bran preparations obtained from untreated wheat grain (compare RMB 5-11 and RMB 10-14 with RMB 0-11 and compare RMB 5-25 and RMB 10-27 with RMB 0-23 in Table 3).

Interestingly, at comparable removal rates, roller milling bran preparations obtained by roller milling of partially debranned grain have substantially higher AX(OS) contents, lower α/β-glucan contents and lower A/X ratios than debranning bran preparations obtained by further debranning of partially debranned grain (compare RMB 5-11 with DBB 5-10 and RMB 10-14 with DBB 10-15 in Table 3).

Production of Soluble AX(OS) Preparations from Bran

Following method was used to produce soluble AX(OS) preparations from each of the nine bran preparations (Table 3) obtained by debranning and/or roller milling of wheat grain. Bran was mixed with water (10 kg/kg bran) and an α-amylase preparation (Termamyl 120LS, Novozymes, Bagsvaerd, Denmark; 250 µL/kg bran). The bran slurry was incubated (90° C., 2 hours) and subsequently filtered. The retentate was washed with warm water (80° C., 5 kg/kg bran) and freeze-dried. The quantity and dry substance content of the retentate and filtrate were determined to have mass balance data of the first extraction step. Subsequently, the retentate of the first extraction was mixed with water (15.67 kg/kg retentate) and an endoxylanase preparation (Multifect CX 12 L, Genencor/Danisco, Palo Alto, USA; 2 mL/kg retentate). After an incubation for 6 hours at 50° C., the retentate slurry was heat-treated (10 min, 90° C.) and then filtered. The filtrate was further clarified by centrifugation (10 000 g, 15 min) and freeze-dried to obtain the soluble AX(OS) preparation. The quantity and dry substance of the soluble AX(OS) preparation were determined to have mass balance data of the second extraction step.

Total saccharide, reducing end saccharide and free monosaccharide contents of the nine soluble AX(OS) preparations were determined by gas-liquid chromatography as described above for the bran preparations. From these results, the AX(OS) content of the soluble AX(OS) preparations was calculated according to formula (a) shown above for the AX(OS) content of the bran preparations. AX(OS) content is considered as a measure of the overall purity of the soluble AX(OS) preparations. AX(OS) average DP and free monosaccharides (MS) content were calculated according to formulae (d) and (e), respectively.

$$AX(OS) \text{ average } DP = \{[\text{arabinose}_{TOT} - \text{arabinose}_{FREE}] + [\text{xylose}_{TOT} - \text{xylose}_{FREE}]\} / [\text{xylose}_{RED} - \text{xylose}_{FREE}] \quad (d)$$

$$\text{free } MS \text{ content} = \text{glucose}_{FREE} + \text{galactose}_{FREE} + \text{mannose}_{FREE} + \text{xylose}_{FREE} + \text{arabinose}_{FREE} \quad (e)$$

In the above formulae, the subscripts TOT, RED and FREE refer to total saccharide, reducing end saccharide and free monosaccharide contents, respectively.

From the mass balance data of the production process and the AX(OS) contents of the soluble AX(OS) preparations and the corresponding bran preparations, following production quality parameters were calculated as follows: preparation yield was calculated as the ratio of the produced amount of dry substance of soluble AX(OS) preparation and the amount of dry substance of bran that was used for this production; AX(OS) yield was calculated as the ratio of the amount of dry substance of AX(OS) in the produced soluble AX(OS) preparation and the amount of dry substance of bran that was used for this production; AX(OS) recovery was calculated as the ratio of the amount of dry substance of AX(OS) in the produced soluble AX(OS) preparation and the amount of dry substance of AX(OS) in the bran that was used for this production.

Properties of the soluble AX(OS) preparations and quality parameters of the production of these preparations from bran are shown in Table 3 for each of the nine different bran preparations.

Table 3 shows that preparation yield and AX(OS) recovery increase for subsequent 5% (w/w) debranning bran fractions of wheat grain (DBB 0-5, DBB 5-10, DBB 10-15). However, in line with lower AX(OS) and higher α/β-glucan contents of the bran, purity of the soluble AX(OS) preparations decreases for subsequent 5% (w/w) debranning bran fractions. As a result, AX(OS) yield is not very different for the different 5% (w/w) debranning bran preparations (Table 3). More importantly, AX(OS) yields of all debranning bran preparations are much lower than those of traditional roller milling bran preparations (RMB 0-11 and RMB 0-23). Furthermore, purities of the soluble AX(OS) preparations made from debranning bran preparations are significantly lower than those of soluble AX(OS) preparations made from traditional roller milling bran preparations (Table 3). Purity of the soluble AX(OS) preparations could be improved by additional washing and/or purification steps. However, this typically leads to higher production costs.

The compositional differences between roller milling bran preparations containing only the "coarse bran" milling fraction and those containing both the "coarse bran" and the "fine bran" milling fractions are reflected in differences in the production of soluble AX(OS) preparations (compare RMB 0-23 with RMB 0-11, RMB 5-25 with RMB 5-11 and RMB 10-27 with RMB 10-14 in Table 3). While inclusion of the "fine bran" milling fraction in the bran preparation only has a minor effect on AX(OS) recovery, preparation yield, AX(OS) yield and purity are substantially reduced.

Unexpectedly, in contrast with debranning bran preparations obtained by debranning alone, roller milling bran preparations obtained by the debranning/roller milling combination have significantly higher AX(OS) yields than traditional roller milling bran preparations (compare RMB 5-11 and RMB 10-14 with RMB 0-11 and compare RMB 5-25 and RMB 10-27 with RMB 0-23 in Table 3). Furthermore, purities of the soluble AX(OS) preparations are similar, despite the lower AX(OS) and higher α/β-glucan contents of the roller milling bran preparations obtained by roller milling of partially debranned grain compared with traditional roller milling bran preparations from untreated grains. This can be explained by the observed remarkable increase of AX(OS) recovery when using a roller milling bran preparation from partially debranned wheat grain (Table 3). It should also be noted that an even higher AX(OS) recovery is observed when 10% bran is removed by partial debranning as compared to 5% bran removal by partial debranning (compare RMB 10-14 with RMB 5-25 and RMB 10-27 with RMB 5-25 in Table 3).

Such increase of AX(OS) recovery is not observed with bran preparations made by further debranning of partially debranned grain (compare RMB 5-11 with DBB 5-10 and RMB 10-14 with DBB 10-15 in Table 3). Instead, AX(OS) recoveries of bran preparations obtained by a two step debranning are even lower than those of traditional rolling milling bran preparations (RMB 0-11 and RMB 0-23, Table 3).

Obviously, as a result of the increase of AX(OS) yield while maintaining purity at comparable levels, the use of roller milling bran from grain that was partially debranned prior to roller milling results in higher preparation yields, as well (Table 3).

Finally it should be noted that despite the strong variations in purity, preparation yield, AX(OS) yield and AX(OS) recovery, only minor variations in the AX(OS) average DP and free MS contents are observed with the different bran preparations of Example 1, except for the relatively high free MS content of the first 5% (w/w) debranner bran preparation (DBB 0-5) (Table 3).

REFERENCES

Andersson R. and Aman P., Cereal arabinoxylan: occurrence, structure and properties, In: Advanced Dietary Fibre Technology (McCleary B. V. and Prosky L., Eds.), Blackwell Science Ltd, Oxford, pp. 301-314, 2001.

Antoine C., Peyron S., Mabille F., Lapierre C., Bouchet B., Abecassis J. and Rouau X., Individual contribution of grain outer layers and their cell wall structure to the mechanical properties of wheat bran, Journal of Agricultural and Food Chemistry 51: 2026-2033, 2003.

Barron C., Surget A. and Rouau X., Relative amounts of tissues in mature wheat (*Triticum aestivum* L.) grain and their carbohydrate and phenolic acid composition, Journal of Cereal Science 45: 88-96, 2007.

Beaugrand J., Chambat G., Wong V. W. K., Goubet F., Remond C., Paes G., Benamrouche S., Debeire P., O'Donohue M. and Chabbert B., Impact and efficiency of GH10 and GH11 thermostable endoxylanases on wheat bran and alkali-extractable arabinoxylans, Carbohydrate Research 339: 2529-2540, 2004.

Benamrouche S., Cronier D., Debeire P. and Chabbert B., A chemical and histological study on the effect of (1-4)-beta-endoxylanase treatment on wheat bran, Journal of Cereal Science, 36: 253-260, 2002.

Broekaert W. F., Courtin C. M., Verbeke K., Van de Wiele T., Verstraete W. and Delcour J. A., Prebiotic and other health-related effects of cereal-derived arabinoxylans, arabinoxylan-oligosaccharides, and xylooligosaccharides, Critical Reviews in Food Science and Nutrition 51: 178-194, 2011.

Carvalheiro F., Esteves, M. P., Parajo J. C., Pereira, H., Girio, F. M., Production of oligosaccharides by autohydrolysis of brewery's spent grain, Bioresource Technology 91: 93-100, 2004.

Cloetens L., De Preter V., Swennen K., Broekaert W. F., Courtin C. M., Delcour J. A., Rutgeerts P. and Verbeke K., Dose-response effect of arabinoxylo-oligosaccharides on gastrointestinal motility and on colonic bacterial metabolism in healthy volunteers, Journal of the American College of Nutrition, 27:512-518, 2008.

Courtin C. M., Van den Broeck H. and Delcour J. A., Determination of reducing end sugar residues in oligo- and polysaccharides by gas liquid chromatography, Journal of Chromatography A 866: 97-104, 2000.

Courtin C. M., Swennen K., Broekaert W. F., Lescroart O., Onagbesan O., Buyse J., Decuypere E., Van de Wiele T., Marzoratti M., Verstraete W., Huyghebaert G. and Delcour J. A., Dietary inclusion of wheat bran arabinoxylooligosaccharides has beneficial nutritional effects on chickens, Cereal Chemistry 85: 607-613, 2008.

Delcour J. A. and Hoseney R. C., Principles of Cereal Science and Technology, AACC International, St. Paul, Minn., U.S.A., 2010.

Femia A. P., Salvadori M., Broekaert W. F., Francois I. E. J. A., Delcour J. A., Courtin C. M. and Caderni G., Arabinoxylan-oligosaccharides (AXOS) reduce preneoplastic lesions in the colon of rats treated with 1,2-dimethylhydrazine (DMH), European Journal of Nutrition 49: 127-132, 2010.

Garrote G., Dominguez H. and Parajo J. C., Autohydrolysis of corncob: study of non-isothermal operation for xylooligosaccharide production, Journal of Food Engineering 52: 211-218, 2002.

Hahn-Hägerdal B., Karhumaa K., Fonseca C., Spencer-Martins I., Gorwa-Grauslund M. F., Towards industrial pentose-fermenting yeast strains, Applied Microbiology and Biotechnology 74:937-953, 2007.

Hemery Y., Rouau X., Lullien-Pellerin V., Barron C. and Abecassis J., Dry processes to develop wheat fractions and products with enhanced nutritional quality, Journal of Cereal Science 46: 327-347, 2007.

Hollmann J. and Lindhauer M. G., Pilot-scale isolation of glucuronoarabinoxylans from wheat bran, Carbohydrate Polymers 59: 225-230, 2005.

Izydorczyk M. S. and Biliaderis C. G., Cereal arabinoxylans: advances in structure and physicochemical properties, Carbohydrate Polymers 28: 33-48, 1995.

Kabel M. A., Carvalheiro F., Garrote G., Avgerinos E., Koukios E., Parajo J. C., Girio F. M., Schols H. A. and Voragen A. G. J., Hydrothermally treated xylan rich by-products yield different classes of xylo-oligosaccharides, Carbohydrate Polymers 50: 47-56, 2002.

Maes C. and Delcour J. A., Alkaline hydrogen peroxide extraction of wheat bran non-starch polysaccharides, Journal of Cereal Science 34: 29-35, 2001.

Maes C., Vangeneugden B. and Delcour J. A., Relative activity of two endoxylanases towards water-unextractable arabinoxylans in wheat bran, Journal of Cereal Science 39: 181-186, 2004.

Ohta T., Semboku N., Kuchii A., Egashira Y. and Sanada H., Antioxidant activity of corn bran cell-wall fragments in the LDL oxidation system, Journal of Agricultural and Food Chemistry 45: 1644-1648, 1997.

Ordaz-Ortiz J. J., Devaux M. F. and Saulnier L., Classification of wheat varieties based on structural features of arabinoxylans as revealed by endoxylanse treatment of flour and grain, Journal of Agricultural and Food Chemistry 53: 8349-8356, 2005.

Palmarola-Adrados B., Choteborska P., Galbe M., Zacchi G., Ethanol production from non-starch carbohydrates of wheat bran, Bioresource Technology 96: 843-850, 2005.

Rose D. J. and Inglett G. E., Two-stage hydrothermal processing of wheat (*Triticum aestivum*) bran for the production of feruloylated arabinoxylooligosaccharides, Journal of Agricultural and Food Chemistry, 58: 6427-6432, 2010.

Sanjust E., Salis A., Rescigno A., Curreli N., Rinaldi A., Xylose production from *durum* wheat bran: enzymic versus chemical methods, Food Science and Technology International 10: 11-14, 2004.

Swennen K., Courtin C. M., Lindemans G. C. J. E., Delcour J. A., Large-scale production and characterisation of wheat bran arabinoxylooligosaccharides, Journal of the Science of Food and Agriculture 86: 1722-1731, 2006.

Van Craeyveld V., Swennen K., Dornez E., Van de Wiele T., Marzorati M., Verstraete W., Delaedt Y., Onagbesan O., Decuypere E., Buyse J., De Ketelaere B., Broekaert W. F., Delcour J. A. and Courtin C. M., Structurally different wheat-derived arabinoxylooligosaccharides have different prebiotic and fermentation properties in rats, The Journal of Nutrition 138: 2348-2355, 2008.

Van Craeyveld V., Dornez E., Holopainen U., Selinheimo E., Poutanen K., Delcour J. A. and Courtin C. M., Wheat bran AX properties and choice of xylanase affect enzymic production of wheat bran-derived arabinoxylan-oligosaccharides, Cereal Chemistry 87: 283-291, 2010.

Vitaglione P., Napolitano A. and Fogliano V., Cereal dietary fibre: a natural functional ingredient to deliver phenolic compounds into the gut, Trends in Food Science and Technology, 19: 451-463, 2008.

Yamada H., Itoh K., Morishita Y. and Taniguchi H., Structure and properties of oligosaccharides from wheat bran, Cereal Foods World 38: 490-492, 1993.

Yuan X. P., Wang J. and Yao H. Y., Antioxidant activity of feruloylated oligosaccharides from wheat bran, Food Chemistry 90: 759-764, 2005.

TABLES

TABLE 1

Feed rates, removal rates and codenames of resulting products at the different steps (debranning passes and sieving steps) of multi-stage debranning of wheat grain in Example 1.

| step | average wheat grain feed rate (kg/h) | removal (% w/w) based on grains at start of step target | removal (% w/w) based on grains at start of step actual | removal (% w/w) based on original grains | codenames of resulting products bran | codenames of resulting products grain |
|---|---|---|---|---|---|---|
| pass 1 | 400.5 | 5.00% | 5.49% | 5.49% | DBB 0-5 | |
| sieving 1 | — | | 2.93% | 2.76% | | DBG 5+ |
| pass 2 | 378.3 | 5.00% | 5.53% | 5.07% | DBB 5-10 | |
| sieving 2 | — | | 4.29% | 3.71% | | DBG 10+ |
| pass 3 | 375.2 | 5.00% | 6.03% | 5.00% | DBB 10-15 | |

TABLE 2

Wheat grain moisture contents, relative quantities of the different milling fractions, and codenames of the selected roller milling bran preparations obtained from the wheat grain samples subjected to roller milling in Example 1.

| wheat grain | wheat grain moisture content before adjustment | wheat grain moisture content after adjustment | wheat grain milling fractions (weight %) coarse bran | wheat grain milling fractions (weight %) fine bran | wheat grain milling fractions (weight %) flour | codenames of resulting bran preparations coarse | codenames of resulting bran preparations coarse + fine |
|---|---|---|---|---|---|---|---|
| untreated | 12.3% | 15.0% | 11.4% | 12.1% | 76.6% | RMB 0-11 | RMB 0-23 |
| DBG 5+ | 13.1% | 14.1% | 5.8% | 14.3% | 80.0% | RMB 5-11 | RMB 5-25 |
| DBG 10+ | 12.6% | 13.5% | 4.0% | 13.5% | 82.5% | RMB 10-14 | RMB 10-27 |

TABLE 3

Properties of the bran preparations of Example 1, properties of the soluble AX(OS) preparations made from these bran preparations and quality parameters of the production of these soluble AX(OS).

| | bran preparation properties AX(OS) content (% dm) | bran preparation properties α/β-glucan content (% dm) | bran preparation properties A/X ratio | soluble AX(OS) preparation properties AX(OS) content (% dm) | soluble AX(OS) preparation properties AX(OS) average DP (%) | soluble AX(OS) preparation properties free MS content (% dm) | production quality parameters preparation yield (%) | production quality parameters AX(OS) yield (%) | production quality parameters AX(OS) recovery (%) |
|---|---|---|---|---|---|---|---|---|---|
| DBB 0-5 | 28.2% | 20.7% | 0.72 | 38.7% | 4.9 | 4.6% | 7.4% | 2.9% | 10.1% |
| DBB 5-10 | 15.5% | 45.8% | 0.58 | 30.3% | 4.3 | 2.0% | 11.1% | 3.4% | 21.6% |
| DBB 10-15 | 9.9% | 58.1% | 0.53 | 21.8% | 5.0 | 1.9% | 14.0% | 3.1% | 30.8% |
| RMB 0-11 | 23.1% | 26.6% | 0.56 | 57.2% | 5.4 | 1.7% | 12.8% | 7.3% | 31.6% |
| RMB 0-23 | 19.7% | 35.1% | 0.58 | 55.9% | 6.0 | 2.2% | 11.3% | 6.3% | 32.0% |
| RMB 5-11 | 24.3% | 26.9% | 0.47 | 60.2% | 5.4 | 1.6% | 14.6% | 8.8% | 36.1% |
| RMB 5-25 | 17.9% | 37.9% | 0.52 | 54.1% | 5.8 | 2.0% | 12.9% | 7.0% | 38.8% |
| RMB 10-14 | 22.5% | 32.2% | 0.46 | 61.0% | 5.6 | 1.7% | 16.8% | 10.3% | 45.7% |
| RMB 10-27 | 15.3% | 45.5% | 0.50 | 56.0% | 6.1 | 2.4% | 11.9% | 6.7% | 43.5% |

The invention claimed is:
1. A method for the extraction and isolation of soluble arabinoxylan products from cereal grain wherein said method comprises
    (i) removing part of an outer layer of whole cereal grains by partial debranning, yielding a first cereal bran and partially debranned cereal grains,
    (ii) roller milling said partially debranned cereal grains and separating said partially debranned cereal grains into a second cereal bran fraction and a cereal flour fraction,
    (iii) fractionating said second cereal bran fraction to remove at least part of the particles smaller than 150 μm and obtaining a bran fraction enriched in particles bigger than 150 μm,
    (iv) mashing at least part of said second cereal bran fraction having a reduced weight fraction of particles smaller than 150 μm in an aqueous solution in order to solubilise and optionally depolymerise at least part of the arabinoxylan contained in said second cereal bran fraction, and
    (v) separating a solubilised fraction comprising at least part of the solubilised soluble arabinoxylan products from an insoluble fraction of said mash.

2. The method according to claim 1 wherein prior to its mashing said second cereal bran fraction is ground to a median particle size of between 250 and 1000 μm.

3. The method according to claim 1 wherein prior to its mashing said second cereal bran fraction is ground to a median particle size of between 250 and 1000 μm and said ground second cereal bran fraction is fractionated in order to remove at least part of the particles smaller than 150 μm.

4. The method according to claim 1 wherein the partial debranning of the whole cereal grains results in the production of an amount of said first cereal bran corresponding to 2 to 15% (w/w) of the original weight of the whole cereal grains.

5. The method according to claim 1 wherein the partial debranning of the whole cereal grains results in the production of an amount of said first cereal bran corresponding to between 5 to 10% (w/w) of the original weight of the whole cereal grains.

6. The method according to claim 1 wherein the partial debranning of the whole cereal grains results in the production of an amount of said first cereal bran corresponding to between 7 to 10% (w/w) of the original weight of the whole cereal grains.

7. The method according to claim 1 wherein the partial debranning of the cereal grains is done by pearling.

8. The method according to claim 1 wherein the cereal grains are wheat grains.

9. The method according to claim 1 wherein an endoxylanase enzyme preparation is added to said aqueous solution used for solubilising and depolymerising at least part of the arabinoxylan contained in said second cereal bran.

10. The method according to claim 1 wherein an endoxylanase enzyme preparation is added to said aqueous solution used for solubilising and depolymerising at least part of the arabinoxylan contained in said second cereal bran fraction and wherein said endoxylanase enzyme preparation comprises an endoxylanase with high selectivity for water-unextractable arabinoxylan.

11. The method according to claim 1 wherein an endoxylanase enzyme preparation is added to said aqueous solution used for solubilising and depolymerising at least part of the arabinoxylan contained in said second cereal bran fraction wherein said endoxylanase enzyme preparation comprises an endoxylanase with high selectivity for water-unextractable arabinoxylan and wherein said endoxylanase enzyme preparation comprises an endoxylanase of the glycosyl hydrolyse family 11.

12. The method according to claim 1 wherein an endoxylanase enzyme preparation is added to said aqueous solution used for solubilising and depolymerising at least part of the arabinoxylan contained in said second cereal bran fraction wherein said endoxylanase enzyme preparation comprises an endoxylanase with high selectivity for water-unextractable arabinoxylan and wherein the duration of the treatment with the endoxylanase enzyme preparation is between 2 and 12 hours.

13. The method according to claim 1 wherein at least part of said second cereal bran fraction is mashed in a first aqueous solution in order to extract and solubilise minerals, starch derived compounds and/or protein derived compounds from said second cereal bran fraction and wherein at least part of the fraction comprising solubilised minerals, starch derived compounds and/or protein derived compounds is separated from the remaining non-solubilised bran material, which is subsequently mashed in a second aqueous solution in order to solubilise and optionally depolymerise at least part of the arabinoxylan contained in said remaining non-solubilised bran material.

14. The method according to claim 13 wherein an enzyme preparation comprising an amylase is added to said first aqueous solution.

15. The method according to claim 13 wherein an enzyme preparation comprising a protease is added to said first aqueous solution.

16. The method according to claim 13 wherein an endoxylanase enzyme preparation is added to said second aqueous solution used for solubilising and depolymerising at least part of the arabinoxylan contained in said remaining non-solubilised bran material.

17. The method according to claim 16 wherein said endoxylanase enzyme preparation comprises an endoxylanase with high selectivity for water-unextractable arabinoxylan.

18. The method according to claim 16 wherein said endoxylanase enzyme preparation comprises an endoxylanase of the glycosyl hydrolyse family 11.

19. The method according to claim 16 wherein the duration of the treatment with the endoxylanase enzyme preparation is between 2 and 12 hours.

20. The method according to claim 1 wherein said soluble arabinoxylan products are either soluble arabinoxylan, arabinoxylan-oligosaccharides, xylose, arabinose, ferulic acid or mixtures of two or more of these compounds.

21. The method according to claim 1 wherein said solubilised fraction comprising soluble arabinoxylan products is further treated by filtration or chromatography or combinations thereof in order to reduce its level of minerals and/or other impurities.

22. The method according to claim 1 wherein said solubilised fraction comprising soluble arabinoxylan products is treated by filtration or chromatography or combinations thereof in order to prepare two or more fractions that differ in free ferulic acid content, arabinose to xylose ratio or average degree of polymerisation of the soluble arabinoxylan products.

23. The method according to claim 1 wherein such solubilised fraction comprising soluble arabinoxylan products is incubated with an enzyme preparation comprising an endoxylanase enzyme in order to decrease the average degree of polymerisation of the soluble arabinoxylan products.

24. The method according to claim 1 wherein such solubilised fraction comprising soluble arabinoxylan products is concentrated in order to increase its dry substance concentration.

25. The method according to claim 1 wherein such solubilised fraction comprising soluble arabinoxylan products is dried or crystallised.

26. The method according to claim 1 wherein such solubilised fraction comprising soluble arabinoxylan products comprises on a dry weight basis at least 40% (w/w) of soluble arabinoxylan products.

* * * * *